US007456127B2

(12) United States Patent
Annis et al.

(10) Patent No.: US 7,456,127 B2
(45) Date of Patent: Nov. 25, 2008

(54) ORGANOALUMINUM CATALYST

(75) Inventors: Ioana Annis, Mundelein, IL (US); Eric P. Wasserman, Hopewell, NJ (US)

(73) Assignee: Union Carbide Chemicals and Plastics Technology Corporation

( * ) Notice: Subject to any disclaimer, the term of this patent is extended or adjusted under 35 U.S.C. 154(b) by 550 days.

(21) Appl. No.: 10/469,758

(22) PCT Filed: Mar. 6, 2002

(86) PCT No.: PCT/US02/06992

§ 371 (c)(1), (2), (4) Date: Feb. 2, 2004

(87) PCT Pub. No.: WO02/098559

PCT Pub. Date: Dec. 12, 2002

(65) Prior Publication Data

US 2004/0142814 A1 Jul. 22, 2004

(51) Int. Cl.
*B01J 3/00* (2006.01)
*C07F 5/06* (2006.01)

(52) U.S. Cl. ....................................... 502/171; 556/182

(58) Field of Classification Search ................. 556/182; 502/171

See application file for complete search history.

(56) References Cited

U.S. PATENT DOCUMENTS

| | | | | |
|---|---|---|---|---|
| 2,762,845 | A | | 9/1956 | Stroh et al. |
| 3,135,705 | A | | 6/1964 | Vandenberg et al. |
| 3,459,688 | A | * | 8/1969 | Hsieh ......................... 528/393 |
| 3,553,182 | A | | 1/1971 | Mueller et al. |
| 3,691,111 | A | | 9/1972 | Takaoka et al. |
| 4,299,944 | A | | 11/1981 | Maeda et al. |
| 4,376,723 | A | | 3/1983 | Wolfe et al. |
| 4,721,817 | A | | 1/1988 | Edwards et al. |
| 4,933,502 | A | | 6/1990 | Edwards et al. |
| 5,280,000 | A | * | 1/1994 | Kakugo et al. .............. 502/121 |

FOREIGN PATENT DOCUMENTS

| | | |
|---|---|---|
| EP | 0 196 569 | 1/1990 |
| EP | 1123930 | 8/2001 |
| WO | WO 0023435 A1 * | 4/2000 |

OTHER PUBLICATIONS

Macromol. Symp. 88, 117-122 (1994); "Novel Catalyst System for the Synthesis of Poly(Alkalene Oxide) with Controlled Molecular Weight". Department of Synthetic Chemistry, University of Tokyo, Japan. Inoue et al.

Journ, of Organometallic Chem. 599 (2000) 200-207; "Alkylaluminophosphonate-catalyzed ring-opening homopolynerization of epichlorohydrin and propylene oxide". Department of Chemistry, University of Louisville, USA. Mason et al.

Pure Appl. Chem A35(3), pp. 427-437 (1998); "Epoxide Polymerization and Copolymerization with . . . ". Division of Polymer Synthesis & Processing, Chem. Dept. Warsaw University of Technology, Poland. Kuran et al.

Macromol. Symp. 88, 191-200 (1994); "Heterogeneous Catalysis for ring opening anionic oligomerisation". Laboratoire de Chimie et Procedes de Polymerisation. C.N.R.S. France. Hamaide et al.

Macromol. 2001, 34, 3159-3175. "Molecular design of single site catalyst precursors for the . . . ". Department of Chemistry, Indiana University, USA. Antelman et al.

Angew. Chem. Ind. Ed. 1998, 37, No. 17. "Highly Eff. Catalytic Meerwein—. . . ". Department of Chemistry, Graduate School of Science, Japan. Ooi et al.

Chem. Abstr. vol. 72, 13337 4h; "Catalyst for polymerization of epoxides". Mitsui Toatsu Chem Co. Heizo et al.

Chem. Abstr. No. 67:82921 "Dyable abrasion-resistant polypropylene fibers". Ichikawa et al. & JP 42 010730, Mitsubishi Rayon Co., 1967.

Pat. Abst. Japan vol. 1998, No. 08 JP 10-077282 (Cosmo Sogo); Kenkyusho: Kk; Cosmo Oil Co Ltd.

XP-02210953 "Advanced Organic Chemistry—Reactions, Mechanism . . . "; 1985 John Wiley & Sons, New York, USA. 3rd Edition, pp. 479-484, "Friedel-Crafts Alkylation".

* cited by examiner

*Primary Examiner*—Rei-tsang Shiao
*Assistant Examiner*—Joseph R Kosack

(57) ABSTRACT

An organoaluminum reaction product of A.) a ligand of the formula I, wherein $R_1$ represents an alkyl, aryl, arylalkyl, or alkylaryl group, a $C_{3-24}$ silyl group, or hydrogen, $R_2$, $R_3$, $R_4$, $R_5$, $R_6$, $R_7$, $R_{12}$, and $R_{13}$ are the same or different and represent an alkyl, aryl, arylalkyl, or alkylaryl group, a $C_{3-24}$ silyl group, halide, or hydrogen, with the proviso that at least one of the groups $R_4$ and $R_{13}$ represents hydrogen, $R_8$ represents an alkoxy, alkyl, aryl, arylalkyl, or alkylaryl group, a $C_{3-24}$ silyl group, halide, hydroxyl radical, or hydrogen, E represents O, S, Se, or Te, and n is an integer from 1 to 4, and B.) an aluminum compound of formula $AlR_9R_{10}R_{11}$, wherein $R_9$ and $R_{10}$ are the same or different and represent $C_{1-20}$ alkyl, aryl, arylalkyl, or alkylaryl group, or hydrogen, and $R_{11}$ is a $C_{1-20}$ alkyl, aryl, arylalkyl, alkylaryl or alkoxy group, hydrogen, or halogen is useful as a polymerization catalyst, particularly for the homopolymerization or copolymerization of an alkylene oxide.

5 Claims, 1 Drawing Sheet

ORGANOALUMINUM CATALYST

The present invention relates to an organoaluminum reaction product and to a polymerization catalyst comprising such reaction product.

BACKGROUND OF THE INVENTION

A wide variety of catalysts have been described for the polymerization of alkylene oxides to produce high molecular weight polymers. Metal-based catalysts are the most common ones. Examples include oxides and/or hydroxides of iron, magnesium, aluminum, and zinc, ammonia-modified amides of calcium, and bimetallic cyanides of zinc and cobalt. Most of these catalysts suffer from several disadvantages including limited molecular weight, inadequate molecular weight control, undesirable coloration and odor of the final polymer, difficulties in removing the catalyst residue from the final polymer, toxic catalyst residue, and product instability.

Aluminum-based catalysts have been known and used for many years.

U.S. Pat. No. 3,135,705 describes a family of catalysts based on alkylaluminum-water, or alkylaluminum-water-bifunctional chelating agent, where one of the functionalities of the chelating agent is OH or SH, and the other contains O, N, or S. Unfortunately, the examples of the patent show that the reaction times with the disclosed catalyst are very long.

U.S. Pat. No. 3,459,688 reports improvements of a catalyst consisting of organoaluminum, a metal salt of a beta-diketone, and water in the presence of an ether compound. Unfortunately, the efficiency of the described catalyst is not sufficient for many applications.

*Chemicals Abstracts* Vol. 72, 1970, Abstract No. 133374h, abstracting Japanese patent application 70 05,786, proposes a binary catalyst system comprising an organoaluminum and an alpha-amino acid N-carboxy anhydride.

The published Japanese patent application JP 57008223 describes the use of porphyrino-organoaluminum complexes as catalysts for homo- and copolymerization of alkylene oxides. However, S. Inoue, T. Aida, H. Sugimoto, C. Kawamura, and M. Kuroki report in *Macromol. Symp.* 1994, 88,117-122; and M. R. Mason, and A. M. Perkins report in *J. Organometallic Chem.* 2000, 599,200-207) that these types of catalysts, even in the presence of polymerization enhancers, are slow, and yield low molecular weight, colored materials.

U.S. Pat. No. 4,376,723 describes a catalyst composition comprised of an alkyl aluminum, a secondary amine, a beta-diketone, and water. The secondary amine could function as a molecular weight adjuster. Unfortunately, high temperatures are required which might not be compatible with low molecular weight alkylene oxides.

U.S. Pat. No. 4,721,817 describes catalysts prepared by contacting phosphorous containing acids with aluminum alcoholates or phenolates, to generate non-ionic surfactants. The molecular weights of the described final products are low.

U.S. Pat. No. 4,933,502 describes catalysts formed by contacting a sulfur-containing acid with alkyl alcoholates or aluminum phenolates. The sulfur atoms in the sulfur-containing components in this patent are hexavalent and are used for the preparation of ethoxylated surfactants.

Kuran, W. et al. (J. Macromol. Sci., *Pure Appl. Chem.* 1998, A35(3), 427-437) report the preparation of (25,27-dimethoxy-p-tert-butylcalix[4]arene-26,28-diolato)aluminum chloride, and its successful use for the homopolymerization of propylene oxide or cyclohexene oxide. The catalyst activity is low and reaction times of weeks are required to obtain low molecular weight homopolymers.

Antelmann et al. describe in Macromolecules Vol. 34, pp. 3159-3175 (2001) a catalyst system for the polymerization of propylene oxide based on a bridged bis(phenolate) ligand attached to two aluminum centers, in which the bridge is an alkylidene group. Unfortunately, such complexes have an insufficient activity in the polymerization of ethylene oxide.

In view of the above-mentioned deficiencies of the known catalysts for the polymerization of alkylene oxides, it is still desirable to find new compounds which are useful as catalysts in the polymerization of alkylene oxides.

SUMMARY OF THE INVENTION

One aspect of the present invention is an organoaluminum reaction product of

A.) a ligand of the formula I, (Formula I)

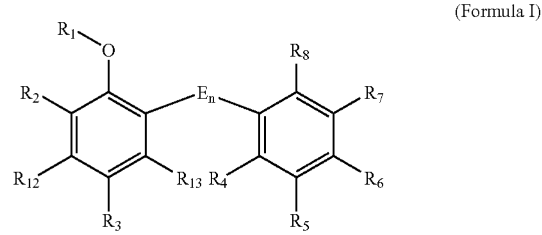

wherein $R_1$ represents an alkyl, aryl, arylalkyl, or alkylaryl group, a $C_{3-24}$ silyl group, or hydrogen, $R_2$, $R_3$, $R_4$, $R_5$, $R_6$, $R_7$, $R_{12}$ and $R_{13}$ are the same or different and represent an alkyl, aryl, arylalkyl, or alkylaryl group, a $C_{3-24}$ silyl group, halide, or hydrogen, with the proviso that at least one of the groups $R_4$ and $R_{13}$ represents hydrogen, $R_8$ represents an alkoxy, alkyl, aryl, arylalkyl, or alkylaryl group, a $C_{3-24}$ silyl group, halide, hydroxyl radical, or hydrogen, E represents O, S, Se, or Te, and n is an integer from 1 to 4, and B.) an aluminum compound of formula $AlR_9R_{10}R_{11}$, wherein $R_9$ and $R_{10}$ are the same or different and represent a $C_{1-20}$ alkyl, aryl, arylalkyl, or alkylaryl group, or hydrogen, and $R_{11}$ is a $C_{1-20}$ alkyl, aryl, arylalkyl, alkylaryl or alkoxy group, hydrogen, or halogen.

Another object of the present invention is an organoaluminum reaction product of A.) a ligand of the formula II, (Formula II)

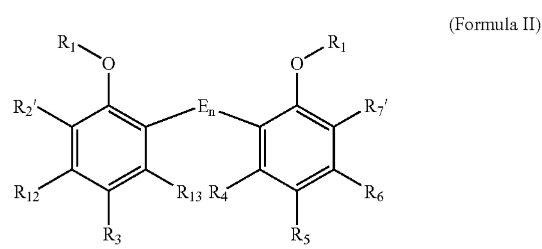

wherein each $R_1$ independently represents an alkyl, aryl, arylalkyl, or alkylaryl group, a $C_{3-24}$ silyl group, or hydrogen, $R_2$' and $R_7$' are the same or different and represent an alkyl, aryl, arylalkyl, or alkylaryl group, a $C_{3-24}$ silyl group, halide, or hydrogen, or $R_2$' and $R_7$' together form a structure of the formula III (Formula III)

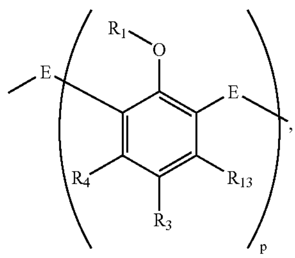

wherein p is an integer from 1 to 8, and $R_1$, $R_3$, $R_4$, $R_5$, $R_6$, $R_{12}$ and $R_{13}$, E and n have the above-mentioned meaning and B.) the above-mentioned aluminum compound.

Another object of the present invention is a process for producing the above-mentioned organoaluminum reaction product.

Yet another aspect of the present invention is a polymerization catalyst comprising the above-mentioned organoaluminum reaction product.

Yet another aspect of the present invention is a process for the homopolymerization or copolymerization of an alkylene oxide.

DETAILED DESCRIPTION OF THE INVENTION

Figure 1:
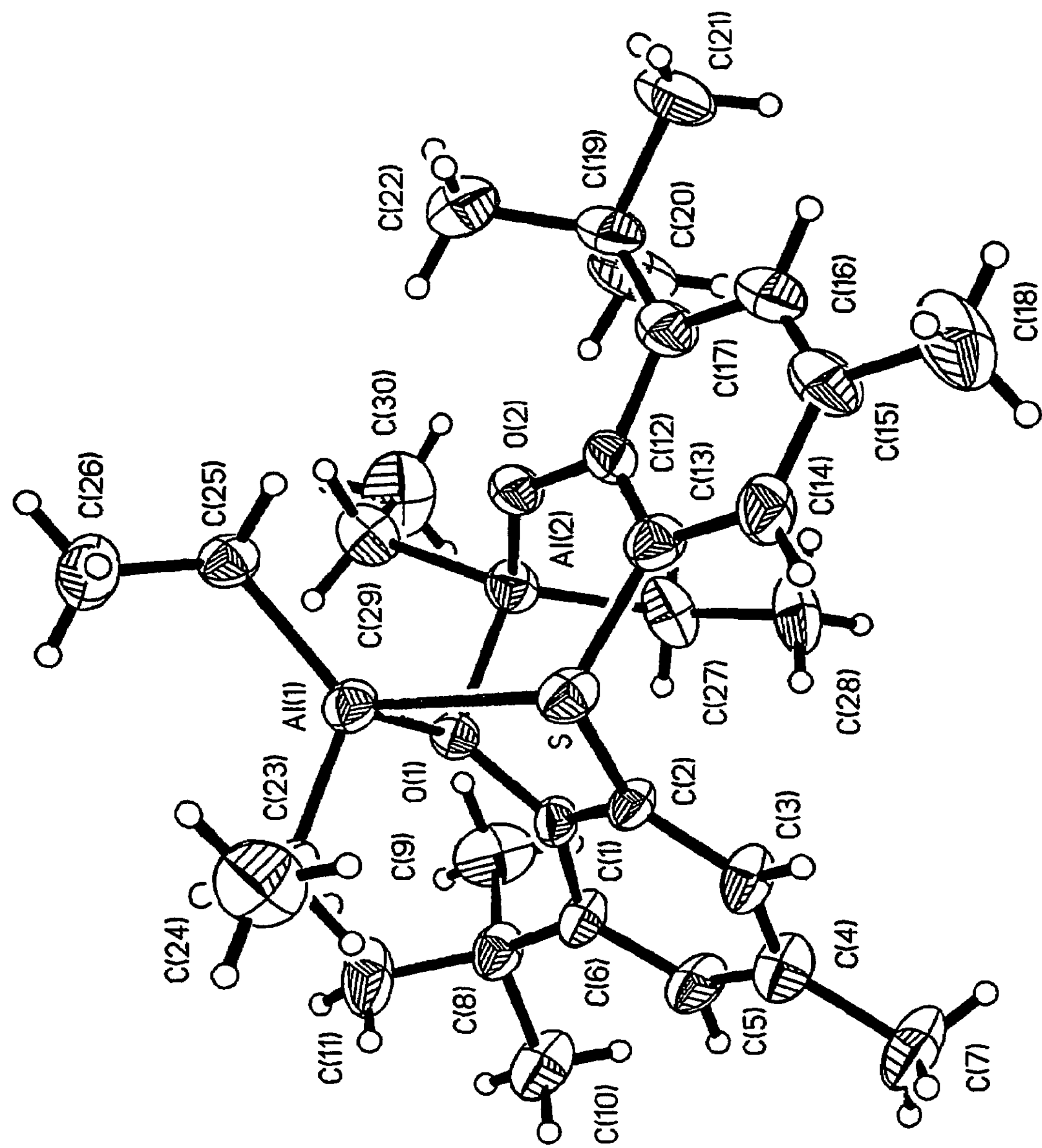
FIG. 1 represents a computer generated model of an organoaluminum reaction product of the invention based on crystal X-ray data.

In a preferred embodiment of the present invention the ligand of the organoaluminum reaction product is a cyclic polyphenol or polyphenol derivative represented by the formula IV (Formula IV)

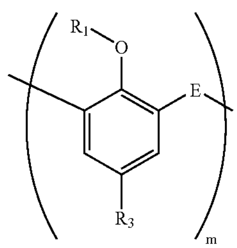

wherein each $R_1$ independently represents an alkyl, aryl, arylalkyl, or alkylaryl group, a $C_{3-24}$ silyl group, or hydrogen, each $R_3$ independently represents an alkyl aryl, arylalkyl, or alkylaryl group, a $C_{3-24}$ silyl group, halide, or hydrogen, each E represents O, S, Se, or Te, and m is an integer from 3 to 10.

In another preferred embodiment of the present invention the ligand of the organoaluminum reaction product is a bridged polyphenol or polyphenol derivative represented by the formula V (Formula V)

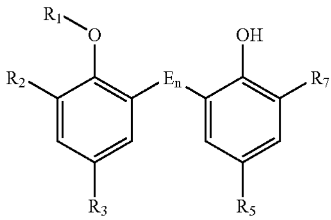

wherein $R_1$ is an alkyl, aryl, arylalkyl, or alkylaryl group, a $C_{3-24}$ silyl group, or hydrogen, $R_2$, $R_3$, $R_5$ and $R_7$ are the same or different and represent an alkyl, aryl, arylalkyl, or alkylaryl group, a $C_{3-24}$ silyl group, halide, or hydrogen, each E represents O, S, Se, or Te, and n is an integer from 1 to 4.

The term "polyphenol or polyphenol derivative" as used herein means compounds with at least two phenyloxy groups.

If one or more of the substituents $R_1$, $R_2$, $R_{2'}$, $R_3$, $R_4$, $R_5$, $R_6$, $R_7$, $R_{7'}$, $R_8$, $R_{12}$ and $R_{13}$ represents an alkyl, arylalkyl or alkylaryl group, the alkyl group or moiety preferably contains from 1 to 8 carbon atoms, more preferably 1, 2, 3 or 4 carbon atoms. The most preferred alkyl moieties are methyl, ethyl or tert-butyl.

The most preferred meaning for $R_1$ is hydroxyl or methyl.

If $R_8$ represents alkoxy, it preferably contains from 1 to 8 carbon atoms, more preferably 1, 2, 3 or 4 carbon atoms. The most preferred alkoxy groups are methoxy or ethoxy.

If one or more of the substituents $R_1$, $R_2$, $R_{2'}$, $R_3$, $R_4$, $R_5$, $R_6$, $R_7$, $R_{7'}$, $R_8$, $R_{12}$ and $R_{13}$ represents an aryl, arylalkyl or alkylaryl group, the aryl group or moiety preferably contains from 6 to 24, more preferably from 6 to 12 carbons.

If one or more of the substituents $R_1$, $R_2$, $R_{2'}$, $R_3$, $R_4$, $R_5$, $R_6$, $R_7$, $R_{7'}$, $R_8$, $R_{12}$ and $R_{13}$ represents a silyl group, the group contains from 3 to 24, preferably from 3 to 9, more preferably from 3 to 6 carbon atoms.

If one or more of the substituents $R_2$, $R_{2'}$, $R_3$, $R_4$, $R_5$, $R_6$, $R_7$, $R_{7'}$, $R_8$, $R_{12}$ and $R_{13}$ represents a halide, it is preferably fluoride or chloride;

n is an integer from 1 to 4, preferably 1 or 2.

In formula III above p is an integer from 1 to 8, preferably from 2 to 3, more preferably 2.

In formula IV above m is an integer from 3 to 10, preferably from 4 to 5, more preferably 4.

The following compounds are illustrative but non-limiting examples of useful ligands:

2,2'-thiobis(6-tert-butyl-4-methylphenol); 2,2'-thiobis(4,6-di-tert-butylphenol); 2,2'-thiobis(4,6-dimethylphenol); 2,2'-thiobis(4,6-bis(1,1,3,3,-tetramethylbutyl)phenol); 2,2'-thiobis(4-methyl-6-(1,1,3,3,-tetramethylbutyl)phenol); 2,2'-thiobis(4,6-dinonylphenol); 2,2'-thiobis(4-methyl-6-nonylphenol); bis(3-tert-butyl-2-hydroxy-5-methylphenyl) disulfide; bis(3,5-di-tert-butyl-2-hydroxyphenyl)disulfide; bis(3-tert-butyl-2-hydroxy-5-methylphenyl)selenide; bis(3,5-di-tert-butyl-2-hydroxyphenyl)selenide; bis(3-tert-butyl-2-hydroxy-5-methylphenyl)telluride; bis(3,5-di-tert-butyl-2-hydroxyphenyl)telluride; (3-tert-butyl-2-ethoxy-5-methylphenyl)(3-tert-butyl-2-hydroxy-5-methylphenyl) sulfide; (3-tert-butyl-2-hydroxy-5-methylphenyl)(3-tert-butyl-2-methoxy-5-methylphenyl)sulfide; (3-tert-butyl-2-hydroxy-5-methylphenyl)(3-tert-butyl-2-n-propoxy-5-methylphenyl)sulfide; (3-tert-butyl-2-hydroxy-5- methylphenyl)(3-tert-butyl-5-methyl-2-t ethylsiloxyphenyl) sulfide; (3,5-di-tert-butyl-2-ethoxyphenyl)(3,5-di-tert-butyl-2-hydroxyphenyl)sulfide; (3,5-di-tert-butyl-2-hydroxyphenyl)(3,5-di-tert-butyl-2-methoxyphenyl)sulfide; (3,5-di-tert-butyl-2-hydroxyphenyl)(3,5-di-tert-butyl-2-trimethylsiloxyphenyl)sulfide; bis(3-tert-butyl-2-methoxy-5-methylphenyl)sulfide; bis(3-tert-butyl-2-ethoxy-5-methylphenyl)sulfide; bis(3-tert-butyl-5-methyl-2-trimethylsiloxyphenyl)sulfide; bis(3-tert-butyl-2-methoxy-5-methylphenyl)sulfide; bis(3,5-di-tert-butyl-2-ethoxyphenyl)sulfide; bis(3,5-di-tert-butyl-2-trimethylsiloxyphenyl)sulfide; (3,5-di-tert-butyl-2-hydroxyphenyl)(2,6-dimethylphenyl) sulfide; tert-butylthiacalix[4]arene; tert-butylthiacalix[5]arene; tert-butylthiacalix[6]arene; tert-butylthiacalix[8]arene; O,O'-dimethyl-tert-butylthiacalix[4]arene; O,O'-diethyl-tert-butylthiacalix[4]arene; O,O"-dimethyl-tert-butylthiacalix[4]arene; O,O"-diethyl-tert-butylthiacalix[4]arene; O,O',O"-trimethyl-tert-butylthiacalix[4]arene; O,O',O",O'"-tetramethyl-tert-butylthiacalix[4]arene; or thiacalix[4]arene.

Preferably, the ligand is (3-tert-butyl-2-ethoxy-5-methylphenyl)(3-tert-butyl-2-hydroxy-5-methylphenyl)sulfide, (3-tert-butyl-2-hydroxy-5-methylphenyl)(3-tert-butyl-2-methoxy-5-methylphenyl)sulfide, (3-tert-butyl-2-hydroxy-5-methylphenyl)(3-tert-butyl-2-n-propoxy-5-methylphenyl) sulfide, (3-tert-butyl-2-hydroxy-5-methylphenyl)(3-tert-butyl-5-methyl-2-trimethylsiloxyphenyl)sulfide or (3,5-di-tert-butyl-2-hydroxyphenyl)(2,6-dimethylphenyl) sulfide. The most preferred ligand is (3-tert-butyl-2-hydroxy-5-methylphenyl)(3-tert-butyl-2-methoxy-5-methylphenyl)sulfide.

The aluminum compound B.) of the organoaluminum reaction product is represented by the formula $AlR_9R_{10}R_{11}$, wherein $R_9$ and $R_{10}$ are the same or different and represent $C_{1-20}$ alkyl, aryl, arylalkyl, or alkylaryl group, or hydrogen, and $R_{11}$ is a $C_{1-20}$ alkyl, aryl, arylalkyl, alkylaryl or alkoxy group, hydrogen, or halogen.

The alkyl group or the alkyl moiety of the arylalkyl, alkylaryl or alkoxy group preferably contains contains from 1 to 8 carbon atoms, more preferably 1 to 6 carbon atoms, most preferably 1, 2, 3 or 4 carbon atoms. The most preferred alkyl moieties are methyl, ethyl, isobutyl, n-hexyl, n-octyl, isoprenyl or tert-butyl.

The aryl group or the aryl moiety of the arylalkyl or alkylaryl group preferably contains from 6 to 12, more preferably 6 or 7 carbons.

If $R_{11}$ is halogen, it is preferably fluorine or chlorine.

The following compounds are illustrative but non-limiting examples of useful aluminum compounds B.): trimethylaluminum; triethylaluminum; triisobutylaluminum; tri-n-hexylaluminum; tri-n-octylaluminum; isoprenylaluminum; tribenzylaluminum; diethylaluminum hydride; diisobutylaluminum hydride; tris(2-cyclohexylethyl)aluminum; diethylaluminum ethoxide; diethylaluminum chloride; or dimethylaluminum chloride. Preferably, the aluminum compound is triisobutylaluminum.

The molar ratio between the aluminum atoms in the aluminum compound B.) and the $OR_1$ groups in the ligand A.) is preferably from about 0.1:1 to about 10:1, more preferably from about 0.2:1 to about 4:1, and most preferably from about 0.5:1 to about 2:1.

The reaction product of the present invention is produced by contacting the chelating ligand A.) and the aluminum compound B.). The combination of the chelating ligand A.) and the aluminum compound B.) can be done in any order. If the ligand A.) contains free phenolic groups, it is advisable to do it carefully, as the reaction of aluminum alkyl compounds with phenols generates heat and alkane. The mixing time is generally between 5 minutes and 24 hours. Preferably, the reaction is conducted under an inert atmosphere, such as dry, deoxygenated nitrogen or argon, in the presence of an aprotic organic reaction diluent, such as a hydrocarbon or an ether, preferably tetrahydrofuran or diethyl ether. Saturated aliphatic, saturated cycloaliphatic or aromatic hydrocarbons are useful, such as butanes, pentanes, hexanes, heptanes, decanes, cyclopentane, cyclohexane, methylcyclohexane, benzene, toluene, xylene or ethylbenzene. A halogenated hydrocarbon with limited reactivity to aluminum alkyl compounds, such as chlorobenzene, can also be used if desired. The weight ratio between the aluminum compound B.) and the organic reaction diluent generally is from 0.01:1 to 4:1, preferably from 0.1:1 to 1:1. It is also useful to attach a bubbler to the reaction apparatus to prevent overpressurization of the reaction vessel, if a light alkane such as ethane is produced. Preferably the concentrations of the reagents in the reaction diluent and their addition rate are kept low enough so that heating in excess of 120° C. is avoided. The preferred reaction temperature is from 0 to 60° C. Advantageously, the produced reaction product is stored and handled in an inert gas atmosphere.

The product of the reaction of the two compounds A.) and B.) may or may not be isolated. If isolated, it may be recovered by removal of reaction diluent under reduced pressure, or by recrystallization. The reaction product may also be an oil at 25° C. The reaction product is generally highly reactive towards water and oxygen, and may be pyrophoric. If the reaction product is not isolated, it is generally stable while it is dissolved in the reaction diluent used for carrying out the reaction of A.) and B.), and can be used in such form. If it is used as a polymerization catalyst, it can for example be added to the polymerization vessel while it is dissolved in the above-mentioned reaction diluent.

It has been found that the reaction product of the ligand A.) and the aluminum compound B.) is useful as a catalyst for the homo- and copolymerization of alkylene oxides. It has been found that the homo- and copolymerization of alkylene oxides to high molecular weight polymers can be carried out efficiently. The catalyst of the invention generally allows for molecular weight control, has reduced pyrophoricity, is compatible with a variety of functional groups, converts to non-toxic residues upon polymerization, and produces odorless products.

While not wishing to be bound by any theory, it is theorized that the function of the chelating ligand A.) is to bring at least two aluminum atoms together in an appropriate geometry for the polymer chain bound to one aluminum atom to attack an alkylene oxide molecule bound to another aluminum atom. Upon extensive investigation the inventors have found that the reaction of alkyl aluminum compounds A.) with bridged ligands B.), where the bridge is formed of oxygen, selenium, tellurium or preferably sulfur, generates catalysts which are very efficient in the polymerization of alkylene oxides. In this regard, it, has been found that the presence of an electron-rich sulfur atom in the ligand gives rise to high polymerization efficiency. It has also been found that replacement of the bridge heteroatom(s) with carbon atoms drastically decreases the catalyst efficiency. Furthermore, it has been found that increasing the valence of the heteroatom(s) results in species with low catalytic activity. It has also been found that the most efficient catalysts have one or more free or protected hydroxyl groups in the ortho position relative to the bridge, allowing for potential cooperative interaction between the two metal binding positions. The organoaluminum reaction products wherein at least two oxygen atoms are bound to phenyl rings at ortho positions relative to the bridging sulfur atom have found to have the highest activity as a catalyst for alkylene oxide polymerization.

The fact that a bridging sulfur atom can coordinate to aluminum is illustrated in FIG. 1, which shows the X-ray crystal structure of bis(3-tert-butyl-2-(diethylaluminoxy)-5-methylphenyl)sulfide (BPS-1-$Al_2Et_4$), a catalyst of the present invention. In this structure, the distance between one of the aluminum atoms (Al1) and the sulfur atom was found to be 2.453(3) Å, indicating bonding.

The polymerization catalyst of the present invention comprises the above described organoaluminum reaction product of the ligand A.) and the aluminum compound B.). This means that either the organoaluminum reaction product is the only component of the polymerization catalyst or other, optional components are also comprised in the polymerization catalyst. Additional, optional components are for example a carrier, such as silica, or a filler, such as fumed silica.

To produce a polymerization catalyst with improved handling properties, the organoaluminum reaction product can be immobilized by impregnation and drying with a porous particulate material such as silica, or by spray-drying a solution of the organoaluminum reaction product, optionally in the presence of a particulate filler such as fumed silica. After the organoaluminum reaction product has been applied on a particulate solid, the immobilized catalyst can either be added directly to a polymerization reactor or can be mixed with an inert fluid, such as mineral oil, and injected as a homogeneous slurry. The weight ratios between these components are preferably chosen that they meet the following relationships:

$$0.1 \leqq (A+B)/(A+B+C) \leqq 10 \text{ and}$$

$$1 \leqq (A+B+C)/(A+B+C+D) \leqq 30,$$

wherein A is the weight of the ligand A.), B is the weight of the aluminum compound B.), C is the weight of the particulate material and D is the weight of the inert fluid.

The activity of the organoaluminum reaction product as polymerization catalyst, particularly as a catalyst for the homopolymerization or copolymerization of an alkylene oxide, can be enhanced by use of a scavenging agent, which remove traces of oxygen or moisture from the polymerization mixture. Scavenging agents with little or no activity towards the polymerization of alkylene oxides are preferred, as they will not broaden the molecular weight distribution of the product. Exemplary of useful scavenging agents are triethylaluminum, triethylborane, and diethylzinc. If a scavenging agent is used, the molar ratio between the scavenging agent and the aluminum atoms in the catalyst generally is from 1:1000 to 1:1, preferably from 1:100 to 1:10.

Certain compounds which are known to enhance the reactivity of metal alkyl complexes, often referred to as "ionizing agents," can be used to further improve the productivity of the inventive catalysts. Examples of ionizing agents are organic boranes and borates, such as triphenylborane, tris(pentafluorophenyl)borane, triphenylcarbenium tetrakis(pentafluorophenyl)borate, triphenylcarbenium tetraphenylborate and N,N-dimethylanilinium tetrakis(pentafluorophenyl)borate. The molar ratio between the ionizing agent and the aluminum atoms in the catalyst generally is from 1:10 to 10:1, preferably from 1:2 to 2:1.

A reaction mixture comprising at least one alkylene oxide is contacted with the above described catalyst to produce polymer. The catalyst is effective for the homo- or copolymerization of a variety of alkylene oxides. Cyclic alkylene oxides are preferred, but the term "alkylene oxide" as used herein also encompasses functionalized alkylene oxides, such as epihalohydrins, glycidyl amines, unsaturated glycidyl ethers, glycidyl acrylates, methacrylates, and glycidyl alkylsilanes. It has been found that the catalyst of the invention is effective in the presence of halogen or alkoxysilyl functionalities and readily polymerizes alkylene oxides containing these fuctionalities. Furthermore, the catalyst of the invention is also very active in the homopolymerization of cyclic alkylene oxides and aliphatic-substituted alkylene oxides, which are usually hindered by steric and conformational factors.

A list of alkylene oxides that may be homopolymerized or copolymerized is disclosed in U.S. Pat. No. 3,135,705, column 1, line 41 to column 2, line 7. This list is incorporated herein by reference. Preferred alkylene oxides are ethylene oxide, propylene oxide, 1,2-cyclohexene epoxide, 1,2-butene epoxide, allyl glycidyl ether, glycidyl methacrylate, epichlorohydrin, 1,3-butadiene diepoxide, styrene oxide, 4-vinyl-1-cyclohexene 1,2-epoxide, 4-(2-trimethoxysilylethyl)-1,2-epoxycyclohexene and 4-vinyl-1-cyclohexene diepoxide. The most preferred alkylene oxide is ethylene oxide. Random copolymers may be produced from the polymerization of mixtures of at least two alkylene oxides. Block copolymers may be produced from the sequential addition of more than one alkylene oxide, in which nearly total consumption of each alkylene oxide takes place prior to the addition of subsequent monomer(s).

Other monomers may be copolymerized with alkylene oxides through the use of the catalyst of the invention. Preferred examples thereof are methyl acrylate, ethyl acrylate, ε-caprolactone, ethylene carbonate, trimethylene carbonate, 1,3-dioxolane, carbon dioxide, carbonyl sulfide, tetrahydrofuran, methyl isocyanate, and methyl isocyanide.

The most preferred alkylene oxide polymer is ethylene oxide homopolymer.

Other preferred alkylene oxide polymers are copolymers of ethylene oxide with epichlorohydrin or copolymers of ethylene oxide with cyclohexene oxide. The molar ratio between epichlorohydrin and ethylene oxide or the molar ratio between cyclohexene oxide and ethylene oxide as monomers in the polymerization medium is generally from 0.0001:1 to 10:1, more preferably from 0.001:1 to 5:1, most preferably from 0.01:1 to 1:1.

If an alkylene oxide copolymer is produced, the produced copolymer generally comprises at least 50 mole percent, preferably at least 70 mole percent, more preferably at least 85 mole percent alkylene oxide units.

The molar ratio between the alkylene oxide and the aluminum atoms in the catalyst generally is from 10:1 to 300,000:1, preferably from 200:1 to 200,000:1, more preferably from 300 to 30,000.

Polymerization of one or more alkylene oxides and optional other comonomers may be performed in the gas phase, solution phase, or in a slurry, generally at pressures from 0.1 to 1000 bar, more preferably from 1 to 100 bar, most preferably from 1 to 15 bar. The polymerization temperature generally ranges from −40° C. to 200° C., although it is highly recommended that the reaction temperature be kept as low as economically practical to avoid spontaneous or runaway polymerization. Preferably, the polymerization is performed at a temperature of from 0° C. to 100° C., more preferably from 10° C. to 60° C.

Preferably, the polymerization is conducted in a slurry of a hydrocarbon. Aromatic hydrocarbons are also useful, such as benzene, toluene, xylene, or ethylbenzene. Preferably, the polymerization is conducted in a slurry of an aliphatic hydrocarbon, preferably a saturated aliphatic or saturated cycloaliphatic hydrocarbon, such as a butane, a pentane, a hexane, a heptane, a decane, cyclopentane, cyclohexane, or methylcyclohexane. Alternatively, the polymerization can be conducted in an ether, such as diethyl ether.

The alkylene oxide as well as any solvent or inert gas should generally be thoroughly dried and deoxygenated prior to use. It is often advantageous to employ an above-mentioned scavenging agent in the reaction medium, which removes the last traces of adventitious water, which might reduce polymerization activity. An above-mentioned ionizing agent can be used to further improve the productivity of the inventive catalyst. Other methods for enhancing polymerization activity which are known to those skilled in the art may also be employed.

To control the molecular weight of the polymer, one may vary the ratio between monomer and catalyst, the number-average molecular weight rising with this ratio. Alternatively, one may use a chain-transfer agent to reduce the molecular weight. Examples of chain-transfer agents which may work in this regard are metal alkoxides such as aluminum triisopropoxide, tetra-n-butyl titanate, tetraethyl silicate, and zirconium tetra-n-butoxide; and organic carbonates, esters, and orthoesters such as ethyl formate, diethyl carbonate, triethyl orthoformate, and trimethyl orthoacetate. It is possible to lower the molecular weight through the addition of a protic reagent such as an alcohol, for example n-butanol, but large ratios of alcohol to aluminum may destroy catalytic activity for the polymerization.

According to the polymerization process of the present invention an alkylene oxide homopolymer or copolymer is produced which generally has a weight average molecular weight of from 1,000 to $10^7$, preferably from 10,000 to $10^7$, more preferably from 20,000 to 8,000,000. A narrow molecular weight distribution $M_w/M_n$, also designated as polydispersity index, is typically achieved. $M_w/M_n$ is generally from 1 to 5, preferably from 1 to 2. The resulting polymers are generally white. By using the catalyst of the present invention, alkylene oxide homopolymers and copolymers with the desired molecular weight can be achieved with efficiencies which are comparable to or greater than the known alkylene oxide catalysts.

The alkylene oxide homopolymers and copolymers can be recovered from the polymerization through known methods. These methods include precipitation of polymer through the addition of a poor solvent, followed by filtration and devolatilization, optionally at elevated temperature and reduced pressure. If catalyst residues are present in high concentration in the final composition, it may be useful to quench these residues through controlled hydrolysis to prevent the residues from adversely affecting polymer performance. It is often advantageous to add one or more additives to the polymer at some point in its recovery. Such additives may confer improved resistance to oxidative, photolytic, or thermal degradation, or may improve the appearance of the final product by preventing discoloration or by enhancing diffuse light reflectance.

The present invention is further illustrated by the following examples which should not be construed to limit the scope of the present invention. All parts and percentages are by weight unless otherwise indicated.

EXAMPLES 1 TO 30 AND COMPARATIVE EXAMPLES A TO F

Materials

The following chemicals were obtained from Aldrich Chemical Company, Inc., and were used without further purification: ethyl-p-toluenesulfonate, 98%; methyl p-toluenesulfonate, 98%; 2,4-di-tert-butylphenol, 99%; 2,4-dimethylphenol, 98%; 4-tert-butylphenol, 99%; anhydrous tetraethylene glycol dimethyl ether, 99.5%; sulfur dichloride, 80%; chlorotrimethylsilane, 99+%; sulfur, 99.98%; sodium hypochlorite solution (available chlorine 10-13%); sodium hydride powder, 95%; triethylaluminum (1 M in hexanes); and triisobutylaluminum (1 M in hexanes).

Epichlorohydrin, 99+%; cyclohexene oxide, 98%; and propylene oxide, 99+% were obtained from Aldrich Chemical Company, Inc., and were dried over $CaH_2$, under a $N_2$ atmosphere, prior to polymerization.

2,2'-Thiobis(6-tert-butyl-4-methylphenol) was obtained from Ciba Specialty Chemicals under the trade name Irganox© 1081. 2,2'-Ethylidenebis(4,6-di-tert-butylphenol) was obtained from Ciba Specialty Chemicals under the trademark Irganox 129.

2,2'-Methylenebis(6-tert-butyl-4-methylphenol) was obtained from R. T. Vanderbilt Company, Inc. under the trademark Vanox MBPC.

4,4'-Thiobis(2-tert-butyl-5-methylphenol) was obtained from Monsanto under the trademark Santonox R.

Ethylene oxide was obtained from ARC Chemical Division Balchem Corporation, Slate Hill, N.Y., and used with no further purification. Silica was obtained from Cabot Corporation Tuscola, Ill.

For ligand synthesis, toluene, diethyl ether, and tetrahydrofuran were passed through a deoxo/sieves train before use, while hexanes were passed through molecular sieves. Triethylaluminum (1.56 mol/L solution in heptane) and triisobutylaluminum (0.865 mol/L solution in hexanes) were obtained from Akzo Nobel. m-Xylene-2-sulfenyl chloride was prepared in a manner analogous to that for 2-mesitylenesulfenyl chloride reported by R. G. Hicks and M. B. Nodwell in J. Am. Chem. Soc., Vol.122, pp. 6746-6753 (2000).

Below described polymerizations were carried out in a glass slurry reactor composed of a jacketed reactor kettle, fitted with an air powered mechanical stirrer, thermometer, jacketed addition funnel, cold finger condenser and gas dispersion tube. The monomer addition was done using a gas tight syringe (Hamilton, Fisher Scientific, Pittsburg, Pa.) and when necessary, a single syringe infusion pump (KD Scientific, Fisher, Pittsburg, Pa.).

The number average and weight average molecular weights were measured by gel permeation chromatography, on a Polymer Liquids PL Aquagel-OH, 16 mm column using 0.05% $NaN_3$ as mobile phase, at a rate of 0.8 mL/min, and an injection size of 200 mL. A Water 590 HPLC isocratic pump was used, together with a Waters 717 Plus Autosampler, and dual detection on a Wyatt Technology Dawn DSP Laser Photometer and a Water 2410 refractive index detector. The results were interpreted by use of WTC-Astra 4.72 software. NMR were done on a Bruker AMX-300 operating at the proton frequency of 300 MHz. The differential scanning calorimetry (DSC) was performed in sealed pans, under helium, on a TA Instruments DSC 2920. The samples were cooled to −100° C., heated to 100° C. at a rate of 10 deg/min, followed by re-cooling to −100° C. and reheating to 100° C., both at a rate of 10 deg/min. The temperature of crystallization ($T_{xtal}$) and the melting temperature $T_m$ were automatically assigned by the instrument software. The percent crystallinity was obtained by comparing the heat of fusion of the sample (peak area of $T_m$) with the heat of fusion for 100% crystalline poly(ethylene oxide).

Abbreviations:
BPS: 2,2'-thiobis(6-tert-butyl-4-methylphenol)
BPS-2: 2,2'-thiobis(4,6-di-tert-butylphenol)
BPS-3: 2,2'-thiobis(4,6-dimethylphenol)
BPS-1-Me: (3-tert-butyl-2-hydroxy-5-methylphenyl)(3-tert-butyl-2-methoxy-5-methylphenyl)sulfide
BPS-1-Me2: bis(3-tert-butyl-2-methoxy-5-methylphenyl) sulfide
BPS-1-Et: (3-tert-butyl-2-ethoxy-5-methylphenyl)(3-tert-butyl-2-hydroxy-5-methylphenyl)sulfide
BPS-1-TMS: (3-tert-butyl-2-hydroxy-5-methylphenyl)(3-tert-butyl-5-methyl-2-trimethylsiloxyphenyl)sulfide.
ArSArOH-1:(3,5-di-tert-butyl-2-hydroxyphenyl)(2,6-dimethylphenyl)sulfide. paraBPS: 4,4'-thiobis(2-tert-butyl-5-methylphenol) (Santanox R)
DTBP: 2,6-di-tert-butylphenol
BPC: 2,2'-Methylenebis(6-tert-butyl-4-methylphenol) (Vanox)
BPEt: 2,2'-Ethylidenebis(4,6-di-tert-butylphenol) (Irganox 129)
BPS=O: bis(3-tert-butyl-2-hydroxy-5-methylphenyl)sulfoxide
Scalix: tert-butylthiacalix[4]arene
THF: tetrahydrofuran
PDI: polydispersity index, corresponding to $M_w/M_n$
PEO: poly(ethylene oxide)

Example 1

Synthesis of 2,2'-thiobis(4,6-di-tert-butylphenol) (BPS-2)

A 500 mL round-bottom flask was charged with stirbar and 31.1 g freshly ground 2,4-di-tert-butylphenol (151 mmol). A reflux condenser and addition funnel were attached and the powder subjected to vacuum for 40 min. To the phenol were then added 175 mL hexanes. A solution of 4.8 mL sulfur dichloride (74 mmol) in 55 mL hexanes was added dropwise at room temperature to the reaction flask with slight bubbling. The reaction mixture was stirred under $N_2$ for about 19 hours at room temperature, then refluxed for another 24 hours. The mixture was allowed to cool and then washed with two 100 mL portions of water. The organic fraction was dried with anhydrous sodium sulfate, filtered, and reduced by rotary evaporation to a yellowish paste. Total crude BPS-2: 32.2 g.

Of this material, 6.2 g were purified by column chromatography (hexanes/toluene volume ratio 7:1), yielding 2.905 g BPS-2. $^1$H NMR ($CDCl_3$), δ (ppm): 7.14 (s), 2H, Ar—H; 6.46 (s), 2H, Ar—H; 1.40 (s), 18H, t-Bu; 1.20 (s), 18H, t-Bu.

Example 2

Synthesis of 2,2'-thiobis(4,6-dimethylphenol) (BPS-3)

A 500 mL round-bottom flask was charged with stirbar, 18.2 mL 2,4-dimethylphenol (151 mmol), and 175 mL hexanes. An addition funnel was attached. At room temperature, a solution of 4.8 mL sulfur dichloride (74 mmol) in 25 mL hexanes were added slowly to the phenol solution, which became yellow, with evolution of gas. One hour after the commencement of addition, the addition funnel was replaced with a reflux condenser and the mixture was refluxed for about 16 hours. After cooling, the mixture was washed with two 100 mL portions of water, the second wash leaving three phases: aqueous, organic, and solid. The organic fraction was removed, and the remaining material was washed with 100 mL hexanes, which dissolved most of the solid. The combined organic fractions were dried over anhydrous sodium sulfate, filtered, and reduced to a thick yellow paste by rotary evaporation. The paste was mixed with 100 mL pentane, and a white, free-flowing powder was recovered: 8.235 g (41% based on sulfur dichloride). $^1$H NMR ($CDCl_3$), δ (ppm): 6.97 (s), 2H, Ar—H; 6.88 (s), 2H, Ar—H; 6.15 (br s), 2H, OH; 2.21 (s), 6H, $CH_3$; 2.17 (s) 6H, $CH_3$.

Example 3

Synthesis of (3-tert-butyl-2-hydroxy-5-methylphenyl)(3-tert-butyl-2-methoxy-5-methylphenyl)sulfide (BPS-1-Me)

To a 500 mL 3-necked round-bottom flask were added, under $N_2$, 10.01 g 2,2'-thiobis(6-tert-butyl-4-methylphenol) (27.9 mmol), stirbar, 100 mL THF, and 1.37 g sodium hydride (57.1 mmol, 2.05 eq.), with generation of gas and heat. After bubbling subsided, a 125 mL addition funnel and reflux condenser with vacuum adapter were attached and the apparatus attached to a $N_2$ bubbler. The mixture was heated to reflux in an oil bath for 1 hour, then a solution of 5.21 g methyl-p-toluenesulfonate (30.0 mol, 1.08 eq.) in 50 mL THF were added dropwise. The mixture, now a cloudy pale-yellow slurry, was refluxed overnight. After cooling, a copious solid settled out. To the slurry were then added hydrochloric acid solution (0.75 N) until the pH was below 2. Next, 500 g of a 20 wt % solution of sodium chloride in water and 200 mL diethyl ether were added and the organic fraction separated. The aqueous fraction was washed with 100 mL diethyl ether and the combined organic fractions were dried over anhydrous sodium sulfate, filtered, and reduced by rotary evaporation to a clear, brown oil. The oil was first purified by column chromatography in hexanes/acetone (40:1 volume ratio), then by recrystallization from ethanol, yielding two crops, with combined weight of 5.67 g (55%). $^1$H NMR ($CDCl_3$), δ (ppm): 7.23 (d, J=1.7 Hz), 1H, Ar—H; 7.13 (d, J=2.0 Hz), 1H, Ar—H; 7.12 (s), 1H, OH; 6.93 (d, J=1.9 Hz), 1H, Ar—H; 6.48 (d, J=2.4 Hz), 1H, Ar—H; 4.00 (s), 3H, $OCH_3$; 2.25 (s), 3H, Ar—$CH_3$; 2.12 (s), 3H, Ar—$CH_3$; 1.37 (s), 18H, t-Bu.

Example 4

Synthesis of (3-tert-butyl-2-ethoxy-5-methylphenyl)(3-tert-butyl-2-hydroxy-5-methylphenyl)sulfide (BPS-1-Et)

Under $N_2$, a 250 mL 3-necked round-bottom flask was charged with stirbar, 10.036 g 2,2'-thiobis(6-tert-butyl-4-methylphenol) (28.0 mmol), and 100 mL THF. To this solution was added 0.685 g sodium hydride (28.5 mmol, 1.02 eq.). An addition funnel and reflux condenser with vacuum adapter were attached and the apparatus placed under $N_2$ bubbler and immersed in an oil bath. The oil bath temperature was raised and the mixture refluxed for 2 hours. While the reaction mixture was still refluxing, a solution of 5.595 g ethyl p-toluenesulfonate (27.9 mmol, 1 eq.) was added over a period of 3 hours. (During this period, an additional 50 mL THF were injected into the flask to make up for solvent apparently lost to a leaky joint.) The thick blue-green slurry with white precipitate was refluxed overnight. Next, the slurry was quenched with 200 mL water and mixed with 200 mL diethyl ether to extract the reaction product. The aqueous phase was washed with a further 50 mL of diethyl ether. The combined organic fractions were dried over anhydrous sodium sulfate, filtered, and reduced to a viscous yellow fluid by rotary evaporation. The material was purified first by column chromatography in hexanes/toluene at a volume ratio of 40:1, with one less-pure fraction recrystallized from ethanol. Three crops were recovered, with a total weight of 5.36 g (50%). $^1$H NMR ($CDCl_3$), δ (ppm): 7.22 (d, J=2.0 Hz), 1H, Ar—H; 7.17 (s), 1H, OH; 7.11 (d, J=2.0 Hz), 1H, Ar—H; 6.93 (d, J=2.0 Hz), 1H, Ar—H; 6.50 (d, J=2.0), 1H, Ar—H; 4.15 (q, J=7.0 Hz), 2H, $CH_2CH_3$; 2.24 (s), 3H, Ar—CH3; 2.12 (s), Ar—CH3; 1.52 (t, J=7.0 Hz), $CH_2CH_3$; 1.36 (s), t-Bu.

Example 5

Synthesis of (3-tert-butyl-2-ethoxy-5-methylphenyl)(3-tert-butyl-2-hydroxy-5-methylphenyl)sulfide (BPS-1-Et)

A 100 mL Schlenk flask was charged with a stirbar, 4.010 g 2,2'-thiobis(6-tert-butyl4-methylphenol) (BPS-1, 11.2 mmol), 25 mL dry toluene, and 0.283 g sodium hydride (11.8 mmol). The thick whitish paste was stirred at ambient temperature for 1.5 hours, then placed in an oil bath set at 130° C. and refluxed for 2 hours. The flask was then removed from heat and allowed to cool. A solution of 2.250 g ethyl p-toluenesulfonate (11.2 mmol) in 15 mL dry toluene was added via cannula into the slurry of deprotonated BPS-1. The flask was returned to the oil bath, where the thick blue-green slurry was allowed to reflux with agitation for another hour, and then allowed to cool slowly overnight. The contents of the flask were then filtered and washed with toluene. Solvent was then removed in vacuo. The desired monoether was separated from small amounts of starting material and diether by column chromatography with a hexanes/methylene chloride solution at a volume ratio of 7:1. A total of 2.264 g BPS-1-Et was recovered (52%). The proton NMR spectrum is similar to that described in Example 4.

Example 6

Synthesis of (3-tert-butyl-2-hydroxy-5-methylphenyl)(3-tert-butyl-5-methyl-2-trimethylsiloxyphenyl) sulfide (BPS-1-TMS)

A round-bottom flask was charged with stirbar, 10.035 g 2,2'-thiobis(6-tert-butyl-4-methylphenol) (28.0 mmol), 5 mL triethylamine (36 mmol, 1.3 equivs.) and 100 mL hexanes. The flask was immersed in an ice-water bath. To this solution was added dropwise a solution of 4.6 mL chlorotrimethylsilane (36 mmol, 1.3 equivs.) in 50 mL hexanes, with the formation of a white precipitate. The slurry was allowed to reach ambient temperature and stirred for three days. The slurry was then filtered twice through a medium glass frit, then washed with 125 mL water. The aqueous solution was then washed with 75 mL hexanes, and the combined organic fractions were dried over anhydrous magnesium sulfate. After filtering, the organic phase was reduced by rotary evaporation to 10.39 g white powder (86%). $^1$H NMR ($CDCl_3$), δ (ppm): 7.14 (m), 2H, Ar—H; 6.90 (s) 1H, Ar—H; 6.73 (s), 1H, OH; 6.31 (m), 1H, Ar—H; 2.25 (s), 3H, Ar—$CH_3$; 2.08, 3H, Ar—$CH_3$; 1.37, 1.38 (two s), 18H, t-Bu; 0.47, 9H, Si—$CH_3$.

Example 7

Synthesis of bis(3-tert-butyl-2-methoxy-5-methylphenyl)sulfide (BPS-1-Me2)

In a glovebox, a three-neck round-bottom flask was charged with stirbar, 1.569 g sodium hydride (65.4 mmol) and 40 mL THF. A reflux condenser with vacuum adapter and an addition funnel were attached and the apparatus was connected to a vacuum line under nitrogen outside the glovebox, and immersed in an oil bath to begin refluxing. To the addition funnel was added a solution of 9.992 g 2,2'-thiobis(6-tert-butyl-4-methylphenol) (27.9 mmol) in 15 mL THF. The BPS-1 solution was added dropwise over a period of five hours while refluxing, and the reaction was continued for three days. To the refluxing slurry of deprotonated BPS-1 was then added a solution of 12.990 g methyl p-toluenesulfonate (69.75 mmol) in 25 mL THF via addition funnel over a period of 2.5 hours. This reaction was continued under reflux for 17 h, then allowed to cool. The slurry was poured into a mixture of 135 g ice and 23 g sodium chloride and then brought to a pH of 3 with the addition of hydrochloric acid. The mixture was poured into a separatory funnel, and extracted with one 100 mL portion and two 65 mL portions of hexanes. The combined organic fractions were dried over anhydrous sodium sulfate, filtered, and reduced to an off-white solid by rotary evaporation. The pure compound was recovered by recrystallization from ethanol. Yield: 8.72 g (81% based on BPS-1). $^1$H NMR ($CDCl_3$), δ (ppm): 7.00 (d, J=2.2 Hz), 2H, Ar—H; 6.74 (d, J=2.2 Hz), 2H, Ar—H; 3.92 (s), 6H, $OCH_3$; 2.17 (s), 6H, Ar—$CH_3$; 1.38 (s), 18H, t-Bu.

Example 8

Synthesis of tert-butylthiacalix[4]arene (Scalix)

The preparation follows that reported by H. Kumagai et al., in Tetrahedron Letters, Vol. 38, No.22, pp. 3971-3972 (1997). A 250 mL round-bottom flask was charged with stirbar, 63.42 g 4-tert-butylphenol (422 mmol), 26.50 g elemental sulfur (827 mmol atomic sulfur), 19 mL tetraethylene glycol dimethyl ether, and 8.60 g sodium hydroxide (215 mmol). A nitrogen stream flowed over the surface of the slurry to help remove hydrogen sulfide, and the effluent gas was bubbled through a concentrated solution of sodium hypochlorite. The reaction temperature was slowly raised to 200° C. over about 4 hours, then heated at 210-240° C. for an additional 6 hours, then allowed to cool slowly. The very dark red solid was broken up in a mixture of toluene and ether at a volume ratio of 1:1. To the slurry were then added 350 mL of an 0.5 M solution of sulfuric acid in water. The organic fraction was separated and the aqueous portion washed with 100 mL of a toluene/ether mixture of a volume ratio of 1:1. The combined organic fractions were reduced by rotary evaporation and vacuum pump to a thick, dark red liquid, to which were added 150 mL hexanes. This precipitated a cream-colored powder which was filtered on medium glass frit and air-dried, yielding 10.6 g (14% based on sulfur). $^1$H NMR ($CDCl_3$), δ (ppm): 9.58 (s), 4H, OH; 7.62 (s), 8H, Ar—H; 1.21 (s), 36H, t-Bu.

Example 9

Synthesis of (3,5-di-tert-butyl-2-hydroxyphenyl)(2,6-dimethylphenyl) sulfide (ArSArOH-1)

Under $N_2$, 2.225 g m-xylene-2-sulfenyl chloride (12.9 mmol) were dissolved in 25 mL hexanes. Under air, a 100 mL 3-necked round-bottom flask was charged with stirbar and 2.64 g 2,4-di-tert-butylphenol (12.8 mmol), then reflux condenser with vacuum adapter and addition funnel were attached. The phenol was dried in vacuo for 20 minutes, then placed under $N_2$ and immersed in an oil bath set at 100° C. The solution of m-xylene-2-sulfenyl chloride was then added via addition funnel and the reaction mixture refluxed overnight. Solvent had evaporated by morning, probably through a leaky joint. The resulting brown solid was ground up in mortar and pestle and recrystallized from ethanol, yielding 2.170 g cream-colored solid which melted at 101-102° C. A second, somewhat darker crop of 0.434 g was recovered from the mother liquor. Combined yield: 59% (based on 2,4-di-tert-butylphenol). $^1$H NMR ($CDCl_3$), δ (ppm): 7.07-7.13 (m), 4H, Ar—H; 6.82 (d, J=2.4 Hz), 1H, Ar—H; 6.28 (s), 1H, OH; 2.41 (s), 6H, $CH_3$; 1.38 (s), 9H, t-Bu; 1.13 (s), 9H, t-Bu.

Example 10

Synthesis of bis(3-tert-butyl-2-(diethylaluminoxy-5-methylphenyl) sulfide (BPS-TEAl)

An oven-dried, 250 mL 2 neck round bottom flask was charged with a stir bar and 2.69 g 2,2'-thiobis(6-tert-butyl-4-methylphenol) (BPS). The flask was placed under vacuum for 1 hour to remove oxygen and other volatiles from the system. Afterwards, the BPS was dissolved in 20 mL of anhydrous $Et_2O$ (diethyl ether), and chilled in an ice-water bath. To the cold solution were added 15 mL of $Et_3Al$ (triethyl aluminum, 1 M in hexanes), and release of ethane was observed. The mixture was stirred for 1 hour in the ice bath and overnight at room temperature. $^1$H NMR ($C_6D_5CD_3$) after in vacuo concentration δ (ppm): 7.23 (d), 2H, Ar—H; 7.16 (d), 2H, Ar—H; 2.09 (s), 6H, Ar—$CH_3$; 1.44 (s), 18H, Ar-tBu; 1.21 (m), 6H; 0.9 (m), 6H; 0.26 (m); 8H.

Example 11

Poly(ethylene oxide) Preparation Catalyzed by BPS-TEAl System

To a dry, $N_2$ flushed reactor were charged 275 mL hexane. The BPS-TEAl (15 mmol Al) solution produced according to Example 10 was injected via oven dried syringe, followed by condensation/addition of 93 mL of ethylene oxide to the jacketed addition funnel. The polymerization was initiated by addition of 3 mL of ethylene oxide, followed by dropwise addition over a 2 h. The reaction was stopped after 5.5 h total reaction time by addition of isopropanol (IPA) to inactivate the catalyst, and removal of excess ethylene oxide to scrubbers under positive $CO_2$ pressure. The pale yellow polymer was discharged, washed with hexane, and dried in vacuo overnight. Yield: 51.9 g (55.8%, efficiency of 3.1 g poly(ethylene oxide)/mmol Al). NMR ($CDCl_3$) δ 3.63 ppm, broad s, poly(ethylene oxide) backbone; 2.16 s, 1.36 d. GPC: $M_w$=49,710, $M_n$=8879, PDI=5.6.

Example 12

Preparation of bis(3-tert-butyl-2-(diisobutylaluminoxy)-5-methylphenyl) sulfide (BPS-TiBA)

An oven-dried, 100-mL 2 neck round bottom flask was charged with a stir bar and 2.326 g 2,2'-thiobis(6-tert-butyl-4-methylphenol) (BPS). The flask was placed under vacuum for 1 hour to remove oxygen and other volatiles from the system. Afterwards, the BPS was dissolved in 15 mL of anhydrous $Et_2O$ (diethyl ether), and chilled in an ice-water bath. To the cold solution were added 15 mL of $iBu_3Al$ (triisobutyl aluminum, 0.865 M in hexanes), and release of ethane was observed. The mixture was stirred for 1 hour in the ice bath and overnight at room temperature. The solution was used directly in the polymerization step.

Example 13

Preparation of Poly(ethylene oxide) using BPS-TiBA Catalyst

To a dry, $N_2$ flushed reactor were charged 250 mL hexane. A solution of BPS-TiBA catalyst (13 mmol Al) was injected via oven dried syringe, followed by condensation/addition of 86.1 g of ethylene oxide to the jacketed addition funnel. The polymerization was initiated by addition of 5 mL of ethylene oxide, followed by dropwise addition of ethylene oxide over 2.5 hours. After 30 seconds induction period fine, white particles started to form. The reaction was stopped after 6.0 hours total reaction time by addition of isopropanol (IPA) to inactivate the catalyst, and removal of excess ethylene oxide to scrubbers under positive $CO_2$ pressure. The white polymer was discharged, washed with hexane, and dried in vacuo overnight. Yield: 77.3 g (89.8%, efficiency of 6.0 g polymer/mmol Al): NMR ($CDCl_3$) δ 3.63 ppm, broad s, poly (ethylene oxide) backbone. GPC: $M_w$=23,140, $M_n$=18,570, PDI=1.25.

Example 14

Preparation of Poly(ethylene oxide-co-epichlorohydrin) using BPS-TiBA Catalyst

To a dry, $N_2$ flushed reactor were charged 300 mL hexane. A solution of BPS-TiBA catalyst (13 mmol Al) was injected via oven dried syringe, followed by condensation/addition of 103 g of ethylene oxide to the jacketed addition funnel. The polymerization was initiated by addition of 10 mL of ethylene oxide, followed by dropwise addition of ethylene oxide over 3.5 hours. After 1-2 minutes induction period fine, white particles started to form. Dropwise addition of 5 mL epichlorohydrin was started at a rate of 2 mL/h. The reaction was stopped after 5.5 hours total reaction time by addition of isopropanol (IPA) to inactivate the catalyst, and removal of excess ethylene oxide to scrubbers under positive $CO_2$ pressure. The white polymer was discharged, washed with hexane, and dried in vacuo overnight. Yield: 77.3 g (75%, efficiency of 5.9 g copolymer/mmol Al). NMR ($CDCl_3$) δ 3.69 ppm, m, —$CH_2Cl$; 3.63 ppm, broad s, poly(ethylene oxide) backbone. GPC: $M_w$=19,000, $M_n$=17,600, PDI=1.07. DSC mp 55.23° C. (slightly trailing peak), crystallization 35.20° C., 64.48% crystalline.

Example 15

Preparation of Poly(ethylene oxide-co-cyclohexene oxide) using BPS-TiBA Catalyst To a dry, $N_2$ flushed reactor were charged 300 mL hexane. A solution of BPS-TiBA catalyst (10 mmol Al) was injected via oven dried syringe, followed by condensation/addition of 90 g of ethylene oxide to the jacketed addition funnel. The polymerization was initiated by addition of 10 mL of ethylene oxide, followed by dropwise addition of ethylene oxide over 3.5 hours. After 1-2 min induction period fine, white particles started to form. 7.2 mL cyclohexene oxide (dry, freshly distilled) were added at this time, and the liquid took on a yellow color. The reaction was stopped after 5.5 hours total reaction time by addition of isopropanol (IPA) to inactivate the catalyst, and removal of excess ethylene oxide to scrubbers under positive $CO_2$ pressure. The white polymer was discharged, washed with hexane, and dried in vacuo overnight. Yield: 51.8 g (53.4%, efficiency of 5.2 g copolymer/mmol Al). NMR ($CDCl_3$) δ 3.63 ppm broad s, poly (ethylene oxide) backbone, 2.21 ppm, m; 1.95 ppm, m, 1.62 ppm, m, 0.95 ppm, m. GPC: $M_w$=28,300, $M_n$=23,700, PDI=1.19. DSC mp 58.99° C., crystallization 36.62° C., 67.33% crystalline.

Example 16

Preparation of Poly(ethylene oxide) using BPS-TiBA Catalyst in the Presence of TEAl as Impurities Scavenger To a dry, $N_2$ flushed reactor were charged 275 mL hexane and 10 mL triethylaluminum (1 M in hexanes). To the chilled addition funnel were added 81.7 g ethylene oxide, followed by addition of 3 mL ethylene oxide to the reactor. A solution of BPS-TiBA catalyst (6 mmol Al) was injected via oven dried syringe, and the remaining ethylene oxide was added dropwise over 3.5 hours. After 4 minutes induction period, fine, white particles started to form. After 6.0 hours total reaction time, the reaction was stopped by addition of isopropanol (IPA) to inactivate the catalyst, and removal of excess ethylene oxide to scrubbers under positive $CO_2$ pressure. The white polymer was discharged, washed with hexane, and dried in vacuo overnight. Yield: 47.0 g (57.5%, efficiency of 7.8 g polymer/mmol BPS-linked Al). NMR ($CDCl_3$) δ 3.63 ppm, broad s, poly (ethylene oxide) backbone. GPC: $M_w$=17,300, $M_n$=15,500, PDI=1.2. DSC mp 60.59° C., crystallization 35.58° C., 72.13% crystalline.

Example 17

Preparation of Bis(3-tert-butyl-2-(diisobutylaluminoxy)-5-methylphenyl) Sulfide Hydrate (BPS-TiBA-$H_2O$)

An oven-dried, 100-mL 2 neck round bottom flask was charged with a stir bar and 1.793 g 2,2'-thiobis(6-tert-butyl-4-methylphenol) (BPS). The flask was placed under vacuum for 1 hour to remove oxygen and other volatiles from the system. Afterwards, the BPS was dissolved in 15 mL of dry hexane, and chilled in an ice-water bath. 10 mL of $iBu_3Al$ (triisobutyl aluminum, 1 M in hexanes) were added at 0° C., and release of ethane was observed. The mixture was stirred for 30 min in the ice-bath, and for 6 hours at room temperature. After 6 hours, the solution was chilled to 0° C., and 90 μL of $H_2O$ were added slowly, over 5 min period. The solution was stirred for 1 hour in the ice-bath and overnight at room temperature. The following morning, the solution was hazy. It was used directly in the polymerization step.

Example 18

Preparation of Poly(ethylene oxide) using BPS-TiBA-$H_2O$ Catalyst

To a dry, $N_2$ flushed reactor were charged 275 mL hexane. A solution of BPS-TiBA-$H_2O$ catalyst (10 mmol Al) was injected via oven dried syringe, followed by condensation/addition of 96.4 g of ethylene oxide to the jacketed addition funnel. The polymerization was initiated by addition of 5 mL of ethylene oxide, followed by dropwise addition of ethylene oxide over 3 hours. After 2 minutes induction period fine, yellowish particles started to form. The polymer became increasingly whiter as the reaction proceeded. After 5 hours total reaction time the reaction was stopped by addition of isopropanol (IPA) to inactivate the catalyst, and removal of excess ethylene oxide to scrubbers under positive $CO_2$ pressure. The white polymer was discharged, washed with hexane, and dried in vacuo overnight. Yield: 21.9 g (22.7%, efficiency of 2.0 g copolymer/mmol Al). NMR ($CDCl_3$) δ 3.63 ppm broad s, poly (ethylene oxide) backbone. GPC: $M_w$=1.5×$10^6$, $M_n$=6.9×$10^5$, PDI=2.3. DSC mp 59.2° C., crystallization 38.22° C., 74.18% crystalline.

Example 19

Preparation of diisobutylaluminoxy-tert-butylthiacalix[4]arene (Scalix-TiBA)

A 250 mL 2-neck round bottom flask was charged with a stir bar and 0.821 g thiacalixarene. The flask was placed under vacuum to remove oxygen and other volatile impurities. Afterwards, the solid was suspended in a mixture of 10 mL toluene and 35 mL $Et_2O$ (diethyl ether), and chilled in an ice-water bath. 5 mL of triisobutylaluminum, 1M solution in hexanes, was added, and the mixture was stirred in the ice bath for 1 hour, and at room temperature overnight. Next day it was a clear light green mixture, which was used as it was in the polymerization step.

Example 20

Preparation of Poly(ethylene oxide) using Scalix-TiBA Catalyst

To a dry, $N_2$ flushed reactor were charged 275 mL hexane. The Scalix-TiBA (5 mmol Al) catalyst solution was injected via oven dried syringe, followed by condensation/addition of 105 mL of ethylene oxide to the jacketed addition funnel. The polymerization was initiated by addition of 10 mL of ethylene oxide, followed by dropwise addition over a 2.5 hours. A 30 seconds induction period was followed by formation of fine, white particles. The reaction was stopped after 5 hour total reaction time by addition of isopropanol (IPA) to inactivate the catalyst, and removal of excess ethylene oxide to scrubbers under positive $CO_2$ pressure. The white polymer was discharged, washed with hexane, and dried in vacuo overnight. Yield: 36.3 g (34.6%, efficiency of 7.3 g poly(ethylene oxide)/mmol Al). NMR ($CDCl_3$) δ 3.63 ppm, broad s, poly (ethylene oxide) backbone. GPC: $M_w$=78,250, $M_n$=59,520, PDI=1.32. DSC mp 63.13° C., crystallization 40.89° C., 64.48% crystalline.

Examples 21 to 30

The catalysts were prepared as described in Examples 10 and 12, using the biphenoxide ligands specified below for each individual case, along with the noted alkyl aluminum compound, in the below given ratio of OH to Al. In the case of Example 30, a ratio of OMe to Al of 1:2 was used. The poly(ethylene oxide) polymerizations were run as described in Examples 11 and 13.

Comparative Example A

Preparation of Bis(3-tert-butyl-2-(diethylaluminoxy)-5-methylphenyl)methylene (BPC-TEAl) and PEO Preparation using this Catalyst The catalyst was prepared as described in Example 10 for BPS-TEAl except that 2,2'-methylene-bis(6-tert-butyl-4-methylphenol) was used in place of 2,2'-thiobis(6-tert-butyl-4-methylphenol). Preparation of PEO with this catalyst following the same procedure as described in Example 11 (PEO preparation catalyzed by BPS-TEAl system) gave an efficiency of 0.44 g PEO/mmol Al, which indicates that replacing the thioether with a methylene group is detrimental to catalyst activity.

Comparative Example B

Preparation of Bis(3-tert-butyl-4-(diethylaluminoxy)-6-methylphenyl) Sulfide (paraBPS-TEAl), and PEO Preparation using this Catalyst The catalyst was prepared as described in Example 10 for BPS-TEAl except that 4,4'-thiobis(2-tert-butyl-5-methylphenol) was used in place of 2,2'-thiobis(6-tert-butyl-4-methylphenol). Preparation of PEO with this catalyst following the same procedure as described in Example 11 (PEO preparation catalyzed by BPS-TEAl system) gave an efficiency of 0.83 g PEO/mmol Al. This indicates that changing the position of the hydroxyl groups from ortho relative to the thioether linkage to para relative to the thioether linkage is detrimental to catalyst activity.

Comparative Example C

Preparation of bis(3-tert-butyl-2-(diisobutylaluminoxy)-5-methylphenyl)sulfoxide (BPS=O-TiBA) and PEO Preparation using this Catalyst The catalyst was prepared as described in Example 12 for BPS-TiBA except that bis(3-tert-butyl-2-hydroxy-5-methylphenyl)sulfoxide was used in place of 2,2'-thiobis(6-tert-butyl-4-methylphenol). Preparation of PEO with this catalyst following the same procedure as described in Example 13 (PEO preparation catalyzed by BPS-TiBA system) gave an efficiency of 1.04 g PEO/mmol Al. This indicates that replacing the sulfur bridge with a sulfoxide bridge is detrimental to catalyst activity.

Comparative Example D

Preparation of 1,1'-bis(3,5-di-tert-butyl-2-diethylaluminoxyphenyl) ethylidine (BPEt-TEAl), and PEO Preparation using this Catalyst The catalyst was prepared as described in Example 10 for BPS-TEAl except that 2,2'-ethylidenebis(4,6-di-tert-butylphenol) was used in place of 2,2'-thiobis(6-tert-butyl-4-methylphenol). Preparation of PEO with this catalyst following the same procedure as described in Example 11 (PEO preparation catalyzed by BPS-TEAl system) gave an efficiency of 0.33 g PEO/mmol Al, which indicates that replacing the thioether with a ethylidene group is detrimental to catalyst activity.

Comparative Example E

Preparation of 2,6-di-tert-butyl-diethylaluminoxybenzene (DTBP-TEAl) and PEO Preparation using this Catalyst Candidate The catalyst was prepared as described in Example 10 for BPS-TEAl except that 2,6-di-tert-butylphenol was used in place of 2,2'-thiobis(6-tert-butyl-4-methylphenol). Preparation of PEO with this catalyst following the same procedure as described in Example 11 ( BPS-TEAl PEO preparation) gave an efficiency of 1.1 g PEO/mmol Al, which indicates that compounds formed by reaction of alkylaluminum with non-bridged monophenoxides have much lower catalytic efficiency than the catalysts of the invention having a bridged ligand.

Comparative Example F

The polymerization was run as described in Examples 11 or 13, except that straight TEAl (1M in hexanes) was used instead of a catalyst of the invention.

In Table I below a direct comparison of the yields and properties of the resulting PEO (ethylene oxide homopolymer) is listed when employing catalysts prepared with various bis(phenolic) and mono(phenolic) ligands and different alkylaluminum reagents

TABLE 1

| Example or Comparative Example | Ligand | Aluminum compound | Ligand:Al | Efficiency g PEO/ mmol Al | $M_w$ | $M_n$ | PDI |
|---|---|---|---|---|---|---|---|
| 10-11 | BPS | $Et_3Al$ | 1:2 | 3.44 | 49,000 | 8,800 | 5.6 |
| 21 | BPS | $Et_3Al$ | 1:4 | 2.28 | 24,000 | 11,000 | 2.2 |
| 22 | BPS | $Et_3Al$ | 1.5:2 | 3.54 | 8,490 | 8,200 | 1.03 |
| 12-13 | BPS | $iBu_3Al$ | 1:2 | 5.96 | 23,140 | 18,570 | 1.25 |
| 23 | BPS | $iBu_3Al$ | 1:1 | 6.8 | 28,260 | 20,980 | 1.35 |
| 24 | BPS-2 | $iBu_3Al$ | 1:2 | 5.2 | 23,800 | 21,700 | 1.09 |
| 25 | BPS-3 | $iBu_3Al$ | 1:2 | 2.2 | 32,400 | 28,800 | 1.13 |
| 26 | BPS-1-Me | $iBu_3Al$ | 1:1 | 15 | 103,700 | 90,390 | 1.15 |
| 27 | BPS-1-Et | $iBu_3Al$ | 1.2:1 | 13.0 | 62,770 | 54,770 | 1.15 |
| 28 | BPS-1-TMS | $iBu_3Al$ | 1:1 | 9.8 | 95,250 | 79,930 | 1.19 |
| 29 | ArSArOH-1 | $iBu_3Al$ | 1:1 | 3.12 | 28,580 | 24,380 | 1.17 |
| 30 | BPS-1-Me2 | $iBu_3Al$ | 1:1 | 4.3 | | | |
| F | — | $Et_3Al$ | | 0.65 | | | |
| B | ParaBPS | $Et_3Al$ | 1:2 | 0.83 | 97,320 | 16,240 | 6 |
| E | DTBP | $Et_3Al$ | 1:1 | 1.1 | | | |
| A | BPC | $Et_3Al$ | 1:2 | 0.44 | 213,000 | 46,100 | 4.6 |

TABLE 1-continued

| Example or Comparative Example | Ligand | Aluminum compound | Ligand:Al | Efficiency g PEO/ mmol Al | $M_w$ | $M_n$ | PDI |
|---|---|---|---|---|---|---|---|
| D | BPEt | $Et_3Al$ | 1:2 | 0.33 | — | — | — |
| C | BPS═O | $iBu_3Al$ | 1:2 | 1.04 | — | — | — |

What is claimed is:

1. A process for the homopolymerization or copolymerization of an alkylene oxide in the presence of an organoaluminum reaction product of A.) a ligand of the formula I, (Formula I)

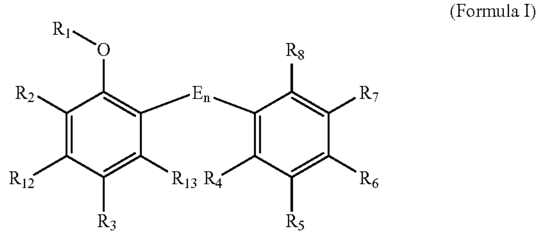

wherein $R_1$, $R_2$, $R_3$, $R_4$, $R_5$, $R_6$, $R_7$, $R_{12}$ and $R_{13}$ are the same or different and represent an alkyl group or hydrogen, with the proviso that at least one of the groups $R_4$ and $R_{13}$ represents hydrogen, $R_8$ represents the hydroxyl radical, E represents sulfur S, and n is 1, and B.) an aluminum compound of formula $AlR_9R_{10}R_{11}$, wherein $R_9$ and $R_{10}$ are the same or different and represent a $C_{1-20}$alkyl, aryl, arylalkyl, or alkylaryl group, or hydrogen, and $R_{11}$ is a $C_{1-20}$alkyl, aryl, arylalkyl, or alkylaryl group, hydrogen, or halogen;

wherein the process comprises the step of contacting a reaction mixture comprising at least one alkylene oxide with the organoaluminum reaction product of the ligand of the formula I and the aluminum compound as a polymerization catalyst.

2. The process according to claim 1 wherein the polymerization is conducted in a slurry of a hydrocarbon.

3. The process according to claim 2 wherein the alkylene oxide is ethylene oxide.

4. The process according to claim 3 wherein ethylene oxide is copolymerized with epichlorohydrin or 1,2-cyclohexene epoxide.

5. The process according to claim 4 wherein the molar ratio between epichlorohydrin and ethylene oxide or the molar ratio between 1,2-cyclohexene epoxide and ethylene oxide is from 0.01:1 to 1:1.

* * * * *